United States Patent [19]

Becher et al.

[11] Patent Number: 4,478,852
[45] Date of Patent: Oct. 23, 1984

[54] UREA DERIVATIVES HAVING A PESTICIDAL ACTIVITY

[75] Inventors: Heinz-Manfred Becher, Bingen; Christo A. Drandarevski, Ingelheim; Sigmund Lust, Darmstadt, all of Fed. Rep. of Germany

[73] Assignee: Celamerck GmbH & Co. KG., Ingelheim am Rhein, Fed. Rep. of Germany

[21] Appl. No.: 377,598

[22] Filed: May 12, 1982

[30] Foreign Application Priority Data

May 22, 1981 [DE] Fed. Rep. of Germany ....... 3120359

[51] Int. Cl.$^3$ ..................... C07C 127/19; A01N 47/28
[52] U.S. Cl. ...................................... 424/322; 564/49; 564/50; 564/52
[58] Field of Search ............................ 564/49, 50, 52; 424/322; 71/98, 103, 105, 120

[56] References Cited

U.S. PATENT DOCUMENTS

| 3,119,682 | 1/1964 | Martin et al. | 71/2.6 |
| 4,280,835 | 7/1981 | Ichiki et al. | 564/52 X |
| 4,376,646 | 3/1983 | Rohr et al. | 71/120 |

FOREIGN PATENT DOCUMENTS

| 0004354 | 1/1980 | Japan | 564/52 |
| 0053259 | 4/1980 | Japan | 564/52 |
| 0076855 | 6/1980 | Japan | 567/52 |
| 921682 | 3/1963 | United Kingdom | 564/52 X |

OTHER PUBLICATIONS

Parg et al., European Patent No. 27,965, published May 6, 1981.

Primary Examiner—Thomas A. Waltz
Attorney, Agent, or Firm—Hammond & Littell, Weissenberger & Dippert

[57] ABSTRACT

The present invention relates to new urea derivatives having pesticidal activity, particularly fungicidal activity. The urea derivatives, according to the invention, have the general formula

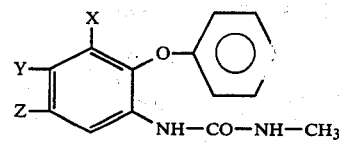

wherein X, Y and Z represent hydrogen or halogen atoms and at least one of the substituents X, Y or Z is a halogen atom.

9 Claims, No Drawings

UREA DERIVATIVES HAVING A PESTICIDAL ACTIVITY

BACKGROUND OF THE INVENTION

The present invention relates to new urea derivatives having pesticidal activity, particularly a fungicidal activity. The urea derivatives according to the invention correspond to the general formula

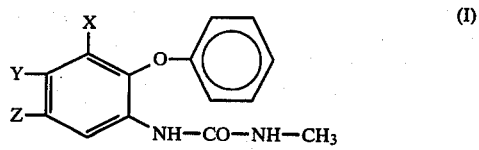
(I)

wherein X, Y and Z represent hydrogen or halogen atoms and at least one of the substituents X, Y or Z represent a halogen atom. If there is more than one halogen atom, they may be the same as or different from one another.

The term halogen atom as used herein refers to fluorine, chlorine bromine. Chlorine and fluorine are preferred. Particularly preferred are compounds of Formula I which contain one to two chlorine atoms and possibly a fluorine atom.

The new urea compounds are prepared by methods which are known such as reactng a suitable aniline with methyl isocyanate or by reacting a suitable isocyanate with methylamine. The reactions for obtaining the ureas of the present invention are carried out in an inert solvent at temperatures between the ambient temperature and that of the boiling temperature of the reaction mixture. Suitable solvents include, for example, aromatic hydrocarbons such as toluene or xylene or ethers such as dioxane or tetrahydrofuran.

The starting materials required for the above described reactions may themselves be prepared according to known general methods. A suitably substituted, usually chlorinated, nitrobenzene is reacted with phenol or with a phenol which has first been reacted with potassium hydroxide. This gives a similarly substituted 2-nitro-diphenyl-ether. This product may be further reacted with potassium fluoride in a solvent if it is desired to replace a chlorine on the ring. The chlorinated or fluorochlorinated 2-nitro-diphenylether may be hydrogenated to give the suitably substituted aniline for reaction with methyl isocyanate or it may be reacted with phosgene to obtain the suitably substituted aniline for reaction with methyl isocyanate or it may be reacted with phosgene to obtain the suiltably substituted isocyanate for reaction with methylamine. These two latter reactions provide the substituted ureas of the present invention.

The compounds of Formula (I) are suitable for use as active ingredients in pesticidal compositions. They are fungicidally active, particularly against the fungi of the genus Tilletia and are particularly suitable as active ingredients in fungicical compositions for the protection of cereal grains from smut.

When they are used for this purpose, they are particularly advantageous because of their favorable ecological characteristics, since the urea compounds made in accordance with the present invention are rapidly degraded to harmless products. The same is not true for other wellknown anti-fungal agents such as pentachloronitrobenzene ("quintozene") whose metabolites such as pentachloroaniline and pentachlorothioanisol are persistent pollutants. Moreover, with the active compounds made according to the present invention, there is no danger of contamination by hexachlorobenzene.

OBJECTS OF THE INVENTION

An object of the present invention is to provide new compounds having pesticidal activity.

A further object of the present invention is to provide compounds having fungicidal activities.

Another object is to provide pesticidal compositions having at least one active ingredient taken from the novel ureas of the present invention.

A further object of the present invention is to provide fungicidal compositions having as an active ingredient at least one of the novel ureas of the present invention.

Another object of the present invention is to provide a method of treating seed grains to protect them from fungus-induced smut.

Another object of the present invention is to provide urea derivatives having fungicidal properties and having the general formula

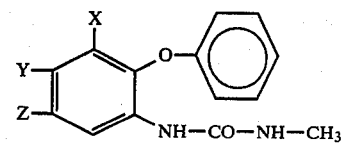

wherein X, Y and Z represent hydrogen or halogen atoms at least one of the substituents X, Y or Z represents a halogen atom.

These and other object of the invention will become more apparent as the description thereof proceeds.

DESCRIPTION OF THE INVENTION

The present invention relates to new urea derivatives having pesticidal activity, particularly fungicidal activity.

The urea derivatives according to the invention correspond to the general formula

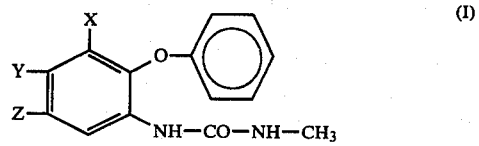
(I)

wherein X, Y and Z represent hydrogen or halogen atoms and at least one of the substituents X, Y or Z represents a halogen atom. If there is more than one halogen atom, they may be the same as or different from one another.

The term halogen atom as used herein refers to fluorine, chlorine and bromine. Chlorine and fluorine are preferred. Particularly preferred are compounds of Formula I which contain one to two chlorine atoms and possibly a fluorine atom in the molecule.

The new urea compounds are prepared by methods which are known:

(1) By reacting the aniline of Formula II with methyl isocyanate

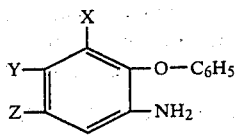

or (2) By reacting an isocyanate of the Formula III with methylamine.

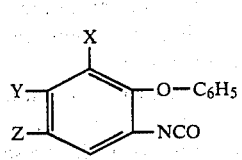

The reactions according to methods (1) and (2) are preferably effected in the presence of an inert solvent at temperatures of between ambient temperature and of the boiling temperature of the reaction mixture. Suitable solvents include, for example, aromatic hydrocarbons such as toluene or xylene or ethers such as dioxane or tetrahydrofuran.

The starting materials can be prepared according to general methods which are known, e.g., according to the following reaction plan:

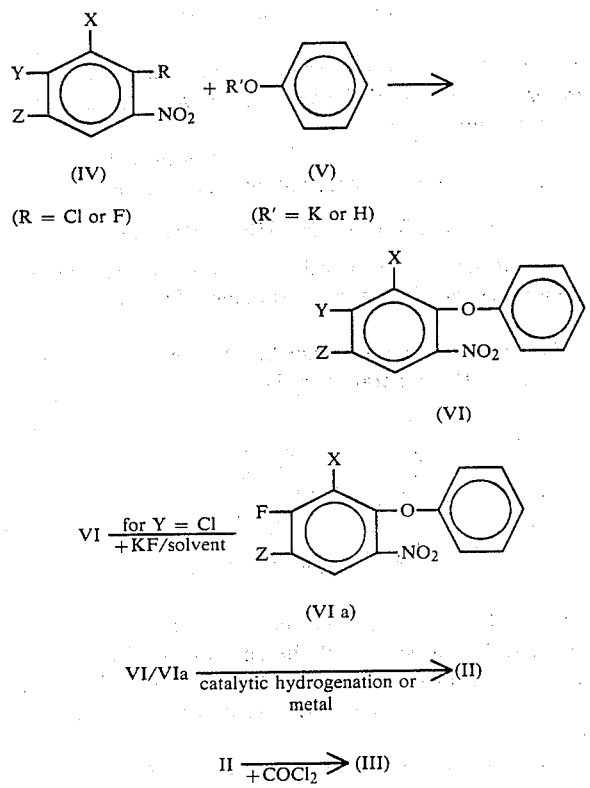

The reaction of (IV) and (V) to form (VI) is effected with potassium phenolate in a solvent (xylene or xylene plus dimethylformamide). The free phenyl (V) is suitable for reaction under the conditions of phase transfer catalysis.

The following examples of the invention are given by way of illustration and not by way of limitation.

EXAMPLES

A. Preparation of Starting Materials 1. 2-Nitro-(mono- or polyhalo)-diphenyl-ether VI (a) 2-nitro-4,5-dichlorodiphenyl-ether (VI) 32 gm of 88% caustic potash (=0.50 mol KOH) are added to a solution of 47 gm (0.50 mol) of phenol in 500 ml of xylene. The mixture thus obtained is boiled, using the water separator, until no more water is separated off. The remaining mixture is left to cool somewhat and 113.5 gm (0.50 mol) of 2,4,5-trichloronitrobenzene, 0.5 gm of Cu powder and 50 ml of dimethylformamide are added. This mixture is refluxed for 8 hours.

The reaction mixture is then left to cool to ambient temperature and stirred with 500 ml of 5% sodium hydroxide solution, to eliminate any unreacted phenol. It is then stirred with water and evaporated (finally in vacuo) to leave a residue. The residual oil is mixed with 100 ml of alcohol and the resulting mixture is cooled in an ice bath. Product (VI) crystallizes out. In order to complete the precipitation, a further 200 ml of petrol are added. The crystalline material is suction filtered 2 hours later, washed with petrol and dried.

Yield: 112 gm (0.395 mol; 79% of theory).

Melting point: 74°–75° C.

(b) The other 2-nitro-(mono- or dichloro)-diphenylethers (VI) are obtained by the same method, using the corresponding dichloro- or trichloronitrobenzenes instead of the 2,4,5-trichloronitrobenzene.

2-nitro-6-chloro-diphenyl ether: oil
2-nitro-4-chloro-diphenyl ether: oil
2-nitro-3,4-dichlorodiphenyl ether: melting point 60°–61° C.

(c) 2-nitro-4-chloro-5-fluoro-diphenyl ether (VI) from 2-nitro-4,5-dichloro-diphenyl ether (VI)

11.6 gm (200 mmols) of anhydrous potassium fluoride are added to a solution of 20 gm (70.4 mmols) of 2-nitro-4,5-dichloro-diphenyl ether (VI) in 70 ml of absolute dimethyl sulfoxide freshly distilled in vacuo. The resulting mixture is stirred at about 130° C. for 8 hours. The reaction mixture is then left to cool and stirred into 400 ml of water. The mixture thus produced is extracted 5 times, each time with 100 ml of isopropyl ether. The combined organic phases are extracted by shaking twice, each time with 100 ml of water, then dried with $MgSO_4$ and evaporated to leave a residue. The partly crystalline residue is stirred at 0° to 3° C. with 40 ml of isopropyl ether. The product which crystallizes out is suction filtered.

Yield: 15.4 gm (58 mmols; 82% of theory).

Melting point: 64°–65° C.

(d) The oily 2-nitro-5-fluoro-4,6-dichloro-diphenylether is obtained from 2-nitro-4,5,6,-trichloro-diphenylether using the method described under (c). This diphenylether can be obtained from vic. tetrachloronitrobenzene using the method described in (a).

2. 2-Phenoxy-(mono- or polyhalo)-aniline (II)

(a) 2-Phenoxy-4,5-dichloroaniline (II).

A mixture of 14.2 gm (50 mmols) of 2-nitro-4,5-dichloro-diphenyl ether (VI), 250 ml of water and 5 ml of glacial acetic acid is heated to boiling, with vigorous stirring. Once the boiling temperature has been reached, 7.5 gm of iron powder is added in small amounts. After all the iron has been added, the mixture is refluxed for a further 6 hours, with vigorous stirring. The reaction mixture is then left to stand for about 15 hours or is centrifuged in a beaker-type centrifuge. Any constituents which have not dissolved in the aqueous phase are thus deposited on the bottom of the vessel. The supernatant aqueous phase is decanted as much as possible. The remaining paste is mixed with about 150 ml of acetone and about 3 gm of kieselguhr and stirred at ambient temperature for one hour. Then the insoluble matter is removed by suction filtering and washed with 100 ml of acetone. The combined acetone solutions are evaporated down to a residue. This residue is mixed with 100 ml of toluene. Its organic constituents dissolve in the toluene. The water remaining forms a separate phase and is removed. The organic phase is evaporated down to a residue.

Crude yield: 12.4 gm (48 mmols; 96% of theory).

The crude product remaining after the solvent has been distilled off is distilled under high vacuum. Purified yield: 11.9 gm (46.5 mmols; 93% of theory).

Boiling point: about 155°–160° C./1.07 mbar.

The distilled product becomes crystalline.

(b) Using the same method, the following anilines were also prepared from the corresponding nitro compounds:

2-phenoxy-3-chloroaniline. Oil; boiling point: about 135°–139° C./14.4 mbar. 2-phenoxy-5-chloroaniline, crystalline; boiling point: about 135°–138° C./1.07 mbar.

1-phenoxy-3,4-dichloroaniline, crystalline; boiling point: about 170°–175° C./1.07 mbar.

2-phenoxy-4-fluoro-3,5-dichloro-aniline. Oil.

3. 2-Phenoxy-(mono- or polyhalo)-phenyl-isocyanate (III)

(a) 2-phenoxy-4,5-dichlorophenyl-isocyanate (III).

At about 5° C., a significant excess of HCl gas is introduced into a solution of 10.16 gm (40 mmols) of 2-phenoxy-4,5-dichloro-aniline (II) in 150 ml of toluene, with stirring. The corresponding hydrochloride is precipitated. Then, at the same temperature, about 10 gm of phosgene are introduced, with stirring. Stirring is then continued for about 15 hours, while the temperature of the reaction mixture is allowed to increase slowly to ambient temperature. It is then slowly heated to 95°–100° C., while stirring is continued. A clear solution is formed. This solution is then stirred for a further 2 hours at 95°–100° C. The excess phosgene is driven off at this temperature by passing nitrogen through the solution. The remaining solution is then concentrated by evaporation under reduced pressure. The oily product is left as the residue.

Yield: 11.2 gm (40 mmols; 100% of theory).

(b) The anilines (II) mentioned under 2(b) were also reacted using the same method to form the corresponding isocyanates (III). The products are all oils.

B. Preparation of the Compounds of Formula I

N-(2-phenoxy-[mono- or polyhalo]-phenyl)-N'-methyl-ureas (I).

EXAMPLE 1

N-(2-phenoxy-4,5-dichlorophenyl)-N'-methyl-urea

About 3 to 4 gm of methylamine gas are introduced into a solution of 7.0 gm (25 mmols) of 2-phenoxy-4,5-dichloro-phenylisocyanate (III) in 70 ml of toluene at ambient temperature. The reaction mixture is then left to stand at ambient temperature for about 15 hours. The product (I) which crystallizes out during this period is then suction filtered, washed with a little toluene and dried.

Yield: 6.2 gm (20 mmols; 80% of theory).

Melting point: 199°–201° C.

The following ureas (I) were also prepared, by the same method, from the corresponding isocyanates (III).

N-(2-phenoxy-3-chlorophenyl)-N'-methyl-urea.
Melting point: 168°–170° C.

N-(2-phenoxy-5-chlorophenyl)-N'-methyl-urea.
Melting point: 147°–149° C.

N-(2-phenoxy-3,4-dichlorophenyl)-N'-methyl-urea.
Melting point: 203°–205° C.

N-(2-phenoxy-4-fluoro-5-chlorophenyl)-N'-methyl-urea.
Melting point: 123°–125° C.

N-(2-phenoxy-4-fluoro-3,5-dichlorophenyl)-N'-methyl-urea.
Melting point: 168°–170° C.

EXAMPLE 2

N-(2-phenoxy-4,5-dichlorophenyl)-N'-methyl-urea 2.0 gm (35 mmols) of methylisocyanate and two drops of triethylamine are added to a solution of 6.35 gm (25 mmols) of 2-phenoxy-4,5-dichloroaniline in 50 ml of anhydrous dioxan. The resulting solution is kept at 50°–60° C. for 15 hours. Then about 40 ml of dioxan are distilled off in vacuo and the residue is stirred with 50 ml of petrol. After cooling to 5°–10° C. for one hour, the crystalline product is suction filtered, washed with 20 ml of petrol and dried.

Yield: 5.9 gm (76% of theory).

Melting point: 197°–199° C.

The effectiveness of the compounds according to the invention is shown in the following Table which gives the results of the Tilletia spore test (1.6 gm of active substance per 100 kg of grains of wheat):

TABLE

| Compound of Formula I | X | Y | Z | Activity in % |
|---|---|---|---|---|
| 1 | Cl | H | H | 99 |
| 2 | H | H | Cl | 99 |
| 3 | Cl | Cl | H | 99 |
| 4 | Cl | F | Cl | 99 |

The compounds according to the invention are combined with conventional excipients and/or carriers in the usual way. The content of active substance may be between about 0.1 and 60% by weight. These fungicidally active compositions used to prevent smut on seed grain usually have a content of active substance of between 0.5 and 20, preferably between 1 and 10% by weight. Examples of such formulations are given hereinafter (in percent by weight).

A. Powder Composition

| A. Powder Composition |
|---|
| 5% active substance according to the invention |
| 95% talc |
| or |
| 5% active substance |
| 5% red pigment dye |
| 90% talc. |

The powder compositions are used in the conventional way, as finely ground mixtures of the ingredients. The quantity of active substance per 100 kg of seed grain, e.g. wheat, is from about 5 to 50 gm.

B. Liquid Composition

Suitable liquid compositions are solutions of the active substances according to the invention in organic solvents such as dimethylformamide, dimethylsulfoxide, ethyleneglycol monomethyl ether, ethyleneglycol dimethyl ether, to which a red dye may be added, if desired. The solutions generally contain between 1 and 10 percent, preferably between about 2 and 5 percent by weight of active substance.

The preceding specific embodiments are illustrative of the practive of the invention. It is to be understood, however, that other expedients known to those skilled in the art or disclosed herein, may be employed without departing from the spirit of the invention or the scope of the appended claims.

We claim:

1. A compound of the formula

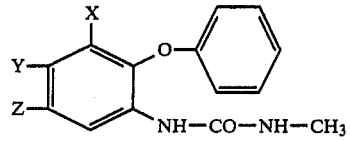

wherein X, Y and Z are each hydrogen or halogen, provided however that at least one of X, Y and Z is halogen.

2. A compound of claim 1, where at least two of X, Y and Z are fluorine, chlorine or bromine. X, Y and Z are fluorine, chlorine or bromine.

3. N-(2-phenoxy-5-chlorophenyl)-N'-methyl urea.

4. N-(2-phenoxy-4,5-dichlorophenyl)-N'-methyl urea.

5. A fungicidal composition consisting essentially of an inert carrier and a fungicidally effective amount of a compound of claim 1.

6. A fungicidal composition of claim 5, where said fungicidally effective amount is 0.1 to 60% by weight, based on the total weight of the composition.

7. A fungicidal composition of claim 5, where said fungicidally effective amount of 0.5 to 20% by weight, based on the total weight of the composition.

8. A fungicidal composition of claim 5, where said fungicidally effective amount is 1 to 10% by weight, based on the total weight of the composition.

9. The method of treating seeds, which comprises contacting said seeds with a fungicidally effective amount of a composition of claim 5.

* * * * *

UNITED STATES PATENT AND TRADEMARK OFFICE
CERTIFICATE OF CORRECTION

PATENT NO. : 4,478,852

DATED : October 23, 1984

INVENTOR(S) : HEINZ-MANFRED BECHER ET AL.

It is certified that error appears in the above-identified patent and that said Letters Patent is hereby corrected as shown below:

Column 1, line 29: "reactng" should read -- reacting --.

Column 8, lines 13 and 14 After the period "." delete

"X, Y and Z are fluorine, chlorine or bromine."

line 2 of Claim 7: Change "of" to -- is --.

Signed and Sealed this

Twenty-first Day of May 1985

[SEAL]

Attest:

DONALD J. QUIGG

Attesting Officer     Acting Commissioner of Patents and Trademarks